US011058899B1

(12) United States Patent
Furukawa et al.

(10) Patent No.: US 11,058,899 B1
(45) Date of Patent: Jul. 13, 2021

(54) SUPERCONDUCTING ELECTROMAGNET APPARATUS AND CHARGED PARTICLE IRRADIATION APPARATUS

(71) Applicant: B dot Medical Inc., Tokyo (JP)

(72) Inventors: Takuji Furukawa, Tokyo (JP); Eri Takeshita, Tokyo (JP); Yousuke Hara, Tokyo (JP)

(73) Assignee: B DOT MEDICAL INC., Tokyo (JP)

( * ) Notice: Subject to any disclaimer, the term of this patent is extended or adjusted under 35 U.S.C. 154(b) by 0 days.

(21) Appl. No.: 17/103,262

(22) Filed: Nov. 24, 2020

(30) Foreign Application Priority Data

Mar. 31, 2020 (JP) .............................. JP2020-063275

(51) Int. Cl.
*A61N 5/10* (2006.01)
*H01F 6/06* (2006.01)
*H05H 7/04* (2006.01)

(52) U.S. Cl.
CPC ............. *A61N 5/1077* (2013.01); *H01F 6/06* (2013.01); *H05H 7/04* (2013.01); *H05H 2007/045* (2013.01)

(58) Field of Classification Search
None
See application file for complete search history.

(56) References Cited

U.S. PATENT DOCUMENTS

| | | | |
|---|---|---|---|
| 6,334,302 B1 * | 1/2002 | Chang-Diaz | F03H 1/0093 60/203.1 |
| 8,593,064 B2 * | 11/2013 | Chang Diaz | H05H 1/46 315/111.61 |
| 8,760,054 B2 * | 6/2014 | DiVergilio | H01J 37/3171 315/111.41 |
| 9,046,270 B2 * | 6/2015 | Weeks | F23R 3/20 |
| 10,249,483 B2 * | 4/2019 | Hosaka | H01J 49/4215 |
| 10,420,202 B2 * | 9/2019 | Matsumoto | H05H 7/02 |
| 10,431,418 B1 * | 10/2019 | Mizushima | H01J 37/141 |
| 10,446,364 B1 * | 10/2019 | Mizushima | H01J 37/3005 |
| 10,804,087 B2 * | 10/2020 | Hosaka | H05H 7/22 |
| 10,881,881 B2 * | 1/2021 | Nonaka | A61N 5/1081 |

(Continued)

FOREIGN PATENT DOCUMENTS

| JP | 2012-11038 A | 1/2012 |
|---|---|---|
| JP | 2018-149179 A | 9/2018 |

(Continued)

OTHER PUBLICATIONS

English Translation of Decision to Grant of JPO issued in Priority Application No. 2020-063275, dated Jun. 30, 2020.

(Continued)

*Primary Examiner* — Amy Cohen Johnson
*Assistant Examiner* — Srinivas Sathiraju
(74) *Attorney, Agent, or Firm* — Birch, Stewart, Kolasch & Birch, LLP

(57) ABSTRACT

The present invention relates to a superconducting electromagnet apparatus having a group of superconducting electromagnets including a first superconducting electromagnet and a second superconducting electromagnet arranged adjacent to the first superconducting electromagnet. Effective magnetic field regions generated by the first and second superconducting electromagnets, respectively, are formed to satisfy predetermined relational equations.

9 Claims, 10 Drawing Sheets

(56) References Cited

U.S. PATENT DOCUMENTS

| | | | | |
|---|---|---|---|---|
| 2008/0006776 A1* | 1/2008 | Furukawa | ................ | G21K 5/04 |
| | | | | 250/396 R |
| 2010/0213384 A1* | 8/2010 | Furukawa | ............ | A61N 5/1043 |
| | | | | 250/396 ML |
| 2011/0084211 A1* | 4/2011 | Yamaya | ............... | A61N 5/1048 |
| | | | | 250/363.03 |
| 2012/0305790 A1* | 12/2012 | Hanawa | ............... | A61N 5/1043 |
| | | | | 250/393 |
| 2012/0305796 A1* | 12/2012 | Iseki | ....................... | A61N 5/10 |
| | | | | 250/396 R |
| 2015/0133714 A1* | 5/2015 | Inaniwa | .................. | G21K 5/04 |
| | | | | 600/1 |
| 2016/0245886 A1* | 8/2016 | McIntyre | ........... | G01R 33/3802 |
| 2017/0113065 A1* | 4/2017 | Inaniwa | ................ | A61B 6/032 |
| 2017/0165502 A1* | 6/2017 | Claereboudt | ............ | H05H 7/04 |
| 2017/0229281 A1* | 8/2017 | Furukawa | .............. | G21K 1/093 |
| 2018/0317311 A1* | 11/2018 | Matsumoto | .............. | H05H 7/02 |
| 2019/0198306 A1* | 6/2019 | Hosaka | .................... | H01J 49/06 |
| 2019/0311878 A1* | 10/2019 | Mizushima | .............. | G21K 5/04 |
| 2019/0311879 A1* | 10/2019 | Mizushima | ............ | G21K 1/093 |
| 2020/0001119 A1* | 1/2020 | Nonaka | .................... | A61N 5/10 |
| 2020/0306563 A1* | 10/2020 | Hara | .................... | A61N 5/1081 |

FOREIGN PATENT DOCUMENTS

| | | |
|---|---|---|
| JP | 2019-180654 A | 10/2019 |
| JP | 2020-779 A | 1/2020 |

OTHER PUBLICATIONS

Korean Notice of Allowance for Korean Application No. 10-2020-0162950, dated Jan. 14, 2021, with English translation.

* cited by examiner

SUPERCONDUCTING ELECTROMAGNET APPARATUS AND CHARGED PARTICLE IRRADIATION APPARATUS

BACKGROUND OF THE INVENTION

Field of the Invention

The present invention relates to a superconducting electromagnet apparatus and a charged particle irradiation apparatus.

Description of the Related Art

Conventionally, particle therapy treatment to irradiate a malignant tumor such as a cancer with a charged particle beam accelerated by high energy and treat the malignant tumor has been employed.

In a particle beam irradiation apparatus disclosed in Japanese Patent Application Laid-Open No. 2013-505757, while an irradiation angle can be selected continuously with respect to an irradiation target, a rotating gantry used for rotating a huge irradiation apparatus is required. Japanese Patent No. 6387476 discloses a charged particle irradiation apparatus that irradiates a target with a charged particle beam from any angle without using a rotating gantry.

When a charged particle beam is deflected by a superconducting electromagnet and converged into the isocenter at a continuous irradiation angle θ, it is required to generate an even magnetic field in a range through which the charged particle beam passes, which results in larger stored energy ($=LI^2/2$, L is inductance, and I is current) than in a case of a typical superconducting electromagnet apparatus. In general, a superconducting electromagnet with large stored energy is required to be designed such that the current is increased to reduce the voltage to an acceptable range, because the voltage when a magnetic field is generated becomes high. Because of a thermal load in cooling a superconducting electromagnet, however, there is a limit in increasing the current, and there is also a limit in reducing the voltage.

If a superconducting electromagnet having relatively large stored energy generates quench (loss of superconducting characteristics), an electric resistance occurs in a superconducting coil of the superconducting electromagnet. When coil current flows therein, a local rise in the temperature occurs, and as a result, the superconducting coil may be damaged. As discussed above, a countermeasure against quench is required for a superconducting electromagnet. As a countermeasure against quench, a protective resistor connected in parallel to a superconducting coil is used, for example. In such a case, the quench voltage occurring at quenching (=protective resistor×stored charge before quenched) is determined by a dump time constant of the superconducting coil L/R (R is a protective resistor, and the dump time constant is a period of current consumption) and stored energy ($LI^2/2$).

In a superconducting electromagnet that generates an even, high magnetic field, since a magnetic flux corresponding to the high magnetic field is required to be confined in the space thereof, the stored energy is larger. Since an increase in stored energy also increases the voltage between terminals of a superconducting coil and the quench voltage occurring at quenching, the stored energy is required to be small as much as possible. Further, in a superconducting electromagnet having large stored energy, a large leakage magnetic field generated from a superconducting coil is also larger.

SUMMARY OF THE INVENTION

Accordingly, the present invention provides a superconducting electromagnet apparatus and a charged particle irradiation apparatus including the same, and the superconducting electromagnet apparatus enables irradiation of a charged particle beam at a continuous irradiation angle θ with respect to the isocenter and reduces stored energy of a superconducting electromagnet compared to a conventional one.

The present invention includes the following aspects [1] to [9]:

[1] A superconducting electromagnet apparatus having a group of superconducting electromagnets including a first superconducting electromagnet and a second superconducting electromagnet arranged adjacent to the first superconducting electromagnet, wherein a pair of superconducting coils of the first superconducting electromagnet, the pair being arranged so as to interpose a path of a charged particle beam, is configured to generate a first effective magnetic field region whose magnetic field faces a direction (Z-axis) orthogonal to a beam direction (X-axis) of a charged particle beam, and an axis orthogonal to both the X-axis and the Z-axis is defined as a Y-axis, wherein a pair of superconducting coils of the second superconducting electromagnet, the pair being arranged so as to interpose a path of a charged particle beam, is configured to generate a second effective magnetic field region whose magnetic field faces the direction (Z-axis) orthogonal to the beam direction (X-axis) of a charged particle beam, wherein an orientation of a magnetic field of the first superconducting electromagnet and an orientation of a magnetic field of the second superconducting electromagnet are the same, wherein the first effective magnetic field region and the second effective magnetic field region are arranged adjacent to each other, and the absolute value of a Y-axis position of the second effective magnetic field region is larger than the absolute value of a Y-axis position of the first effective magnetic field region, (i) wherein for the first effective magnetic field region, on an XY plane, a charged particle beam deflected at a deflection angle φ relative to the X-axis at a deflection point Q and entering the first effective magnetic field region is deflected by the first effective magnetic field region and irradiates an isocenter at an irradiation angle θ relative to the X-axis, an arbitrary point P2 on a boundary defining the first effective magnetic field region and located on an exit side of a charged particle beam is positioned at an equal distance $r_1$ from the isocenter, the point P2 and a point P1 on a boundary defining the first effective magnetic field region and located on an incident side of a charged particle beam are on an arc of a circle of a radius $r_2$ and a central angle (θ+φ), and a distance R between the deflection point Q and the point P1 satisfies relational Equation (4), where a distance between the deflection point Q and the isocenter is denoted as L:

$$R = \sqrt{L^2 + r_1^2 - 2L(r_1\cos\theta + r_2\sin\theta)}, \quad (4)$$

and (ii) wherein for the second effective magnetic field region, on the XY plane, a charged particle beam deflected at a deflection angle $\phi$ relative to the X-axis at a deflection point Q and entering the second effective magnetic field region is deflected by the second effective magnetic field region and irradiates the isocenter at an irradiation angle $\theta$ relative to the X-axis, an arbitrary point P4 on a boundary defining the second effective magnetic field region and located on an exit side of a charged particle beam is positioned at the equal distance $r_1$ from the isocenter, the point P4 and a point P3 on a boundary defining the second effective magnetic field region and located on an incident side of a charged particle beam are on an arc of a circle of a radius $r_3$ and a central angle $(\theta+\phi)$, and a distance R between the deflection point Q and the point P3 satisfies relational Equation (4a):

$$R = \sqrt{L^2 + r_1^2 - 2L(r_1\cos\theta + r_3\sin\theta)}. \quad (4a)$$

[2] The superconducting electromagnet apparatus according to [1], wherein when a deflection angle $\phi$ determined by the point P1 and the deflection point Q, the point P1 being included in the first effective magnetic field region and located at a position closest to the second effective magnetic field region side, is denoted as $\phi_{max}$, and an irradiation angle $\theta$ of a charged particle beam, which enters the first effective magnetic field region at the deflection angle $\phi_{max}$, to the isocenter is denoted as $\theta_{max}$, on the XY plane, the second effective magnetic field region is inclined, with respect to the first effective magnetic field region, at an angle $\psi=(\theta_{max}-\phi_{max})/2$ relative to the X-axis and arranged adjacent to the first effective magnetic field region.

[3] The superconducting electromagnet apparatus according to [1] or [2], wherein an inductance of the first superconducting electromagnet and an inductance of the second superconducting electromagnet are the same.

[4] The superconducting electromagnet apparatus according to any one of [1] to [3], wherein a magnetic pole is embedded inside a superconducting coil of the first superconducting electromagnet or inside a superconducting coil of the second superconducting electromagnet.

[5] The superconducting electromagnet apparatus according to any one of [1] to [4], wherein the second effective magnetic field region partially overlaps the first effective magnetic field region.

[6] The superconducting electromagnet apparatus according to any one of [1] to [4], wherein the group of superconducting electromagnets further has a third superconducting electromagnet arranged adjacent to the second superconducting electromagnet, wherein a pair of superconducting coils of the third superconducting electromagnet, the pair being arranged so as to interpose a path of a charged particle beam, is configured to generate a third effective magnetic field region whose magnetic field faces the direction (Z-axis) orthogonal to the beam direction (X-axis) of a charged particle beam, wherein an orientation of a magnetic field of the second superconducting electromagnet and an orientation of a magnetic field of the third superconducting electromagnet are the same, wherein the second effective magnetic field region and the third effective magnetic field region are arranged adjacent to each other, and the absolute value of a Y-axis position of the third effective magnetic field region is larger than the absolute value of a Y-axis position of the second effective magnetic field region, (iii) wherein for the third effective magnetic field region, on the XY plane, a charged particle beam deflected at a deflection angle $\phi$ relative to the X-axis at a deflection point Q and entering the third effective magnetic field region is deflected by the third effective magnetic field region and irradiates the isocenter at an irradiation angle $\theta$ relative to the X-axis, an arbitrary point P6 on a boundary defining the third effective magnetic field region and located on an exit side of a charged particle beam is positioned at the equal distance $r_1$ from the isocenter, the point P6 and a point P5 on a boundary defining the third effective magnetic field region and located on an incident side of a charged particle beam are on an arc of a circle of a radius $r_4$ and a central angle $(\theta+\phi)$, and a distance R between the deflection point Q and the point P5 satisfies relational Equation (4b):

$$R = \sqrt{L^2 + r_1^2 - 2L(r_1\cos\theta + r_4\sin\theta)}, \quad (4b)$$

and wherein the second effective magnetic field region partially overlaps the first effective magnetic field region and the third effective magnetic field region.

[7] The superconducting electromagnet apparatus according to any one of [1] to [6] further comprising:

two or more power supply configured to supply current to and excite the first and second superconducting electromagnets; and a switching device that switches current supply from the power supply between the first and second superconducting electromagnets in accordance with the irradiation angle $\theta$.

[8] A charged particle irradiation apparatus including the superconducting electromagnet apparatus according to any one of [1] to [7].

[9] The charged particle irradiation apparatus according to [8] further including a bending magnet that deflects a charged particle beam from an accelerator at a deflection angle $\phi$ that is larger than or equal to 10 degrees at the deflection point Q.

DESCRIPTION OF THE EMBODIMENTS

First Embodiment

Figure 1:
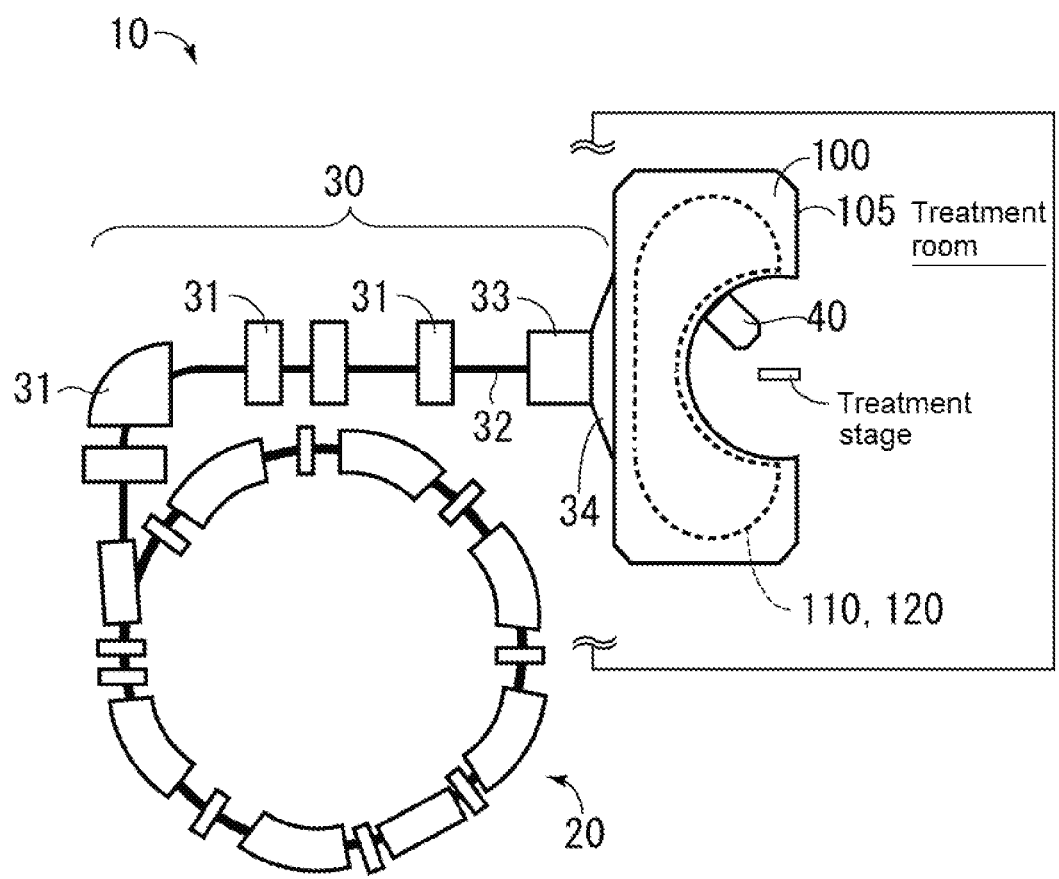
FIG. 1 is a schematic diagram of a configuration of a charged particle irradiation apparatus.

FIG. 1 is a schematic diagram of a configuration of a charged particle irradiation apparatus 10 having a superconducting electromagnet apparatus 100 according to a first embodiment of the present invention. The charged particle irradiation apparatus 10 has the superconducting electromagnet apparatus 100. The charged particle irradiation apparatus 10 may further have an accelerator 20, a charged particle beam transport system 30, and an irradiation nozzle 40. The irradiation nozzle 40 is arranged inside a treatment room provided with a treatment stage on which a patient is placed.

Groups of superconducting electromagnets 110 and 120 of the superconducting electromagnet apparatus 100 are included in a cryostat 105. The inside of the cryostat 105 is maintained at a cryogenic temperature. It may be preferable to maintain the effective magnetic field region in a vacuum as much as possible while maintaining the superconducting state of the superconducting electromagnet apparatus 100 through which a charged particle beam passes. A refrigerant used in the cryostat 105 may be, for example, a helium gas, liquid helium, liquid nitrogen, or the like.

The accelerator 20 is an apparatus that generates a charged particle beam and may be, for example, a synchrotron, a cyclotron, or a linear accelerator. A charged particle beam generated by the accelerator 20 is guided to the superconducting electromagnet apparatus 100 via the charged particle beam transport system 30.

The charged particle beam transport system 30 includes one or a plurality of charged particle beam adjustment units 31, a vacuum chamber 32, a bending magnet 33, a sector-shaped vacuum chamber 34, and the like. The accelerator 20, the charged particle beam adjustment units 31, and the bending magnet 33 are connected via the vacuum chambers 32, and the bending magnet 33 and the superconducting electromagnet apparatus 100 are connected via the sector-shaped vacuum chamber 34. With the sector-shaped vacuum chamber 34 on the XY plane (see FIG. 2) being shaped in a sector, a charged particle beam even deflected at a deflection angle ϕ that is larger than or equal to 10 degrees is able to pass inside the vacuum chamber, and this enables a reduction in the size and a reduction in the installation space compared to a rectangular vacuum chamber.

A charged particle beam is generated by the accelerator 20 on the upstream side, travels inside the vacuum chambers 32 and 34 to avoid or reduce attenuation, and is guided to the superconducting electromagnet apparatus 100 on the downstream side while being adjusted by the charged particle beam adjustment unit 31.

The charged particle beam adjustment unit 31 includes a beam slit used for adjusting the beam shape and/or the dose of a charged particle beam, an electromagnet used for adjusting the beam direction of the charged particle beam, a quadrupole electromagnet used for adjusting the beam shape of the charged particle beam, a steering electromagnet used for finely adjusting the beam position of the charged particle beam, and the like if necessary in accordance with the specification.

The path from the bending magnet 33 for a charged particle beam to the isocenter O (an affected part of a patient) differs in accordance with the irradiation angle θ described later. Because of this, an optical element to which a charged particle beam is subjected may also change in accordance with the irradiation angle θ, and the beam shape of the charged particle beam at the isocenter O may change in accordance with the irradiation angle θ. To cope with this, for example, the charged particle beam adjustment unit 31 provided on the upstream side of the superconducting electromagnet apparatus 100 may be controlled on an irradiation angle θ basis to perform adjustment so as to have a suitable beam shape of the charged particle beam at the isocenter O.

The bending magnet 33 is configured to continuously deflect a charged particle beam at the deflection angle ϕ described later and launch the charged particle beam to the superconducting electromagnet apparatus 100. The superconducting electromagnet apparatus 100 is configured to receive an incident charged particle beam and continuously change the irradiation angle θ of a charged particle beam traveling to the isocenter O in accordance with the deflection angle ϕ.

The irradiation nozzle 40 is located inside a treatment room in which treatment using a charged particle beam or the like are performed and continuously moved so as to be along the shape on the exit side (boundary shape) of an effective magnetic field region generated by the groups of superconducting electromagnets 110 and 120 on the XY plane. The charged particle beam traveling from the exit side of the effective magnetic field region to the isocenter O passes inside the irradiation nozzle 40, and the beam direction or the like of the charged particle beam is finely adjusted by the irradiation nozzle 40.

The irradiation nozzle 40 has a scanning magnet, a beam monitor, and an energy modulation unit (all of which are not illustrated). The scanning magnet adjusts the amount of flowing current or the direction of current, thereby, finely adjusts the beam direction of a charged particle beam launched from the irradiation nozzle 40, and enables a scan of a charged particle beam within a relatively narrow range. The beam monitor monitors a charged particle beam and measures the position of a dose monitor or a beam and the flatness thereof. The energy modulation unit adjusts the energy of a charged particle beam to adjust the depth in a patient reached by the charged particle beam. The energy modulation unit is, for example, a range modulator, a scattering object, a ridge filter, a patient collimator, a patient bolus, an applicator, or a combination thereof.

Figure 2:
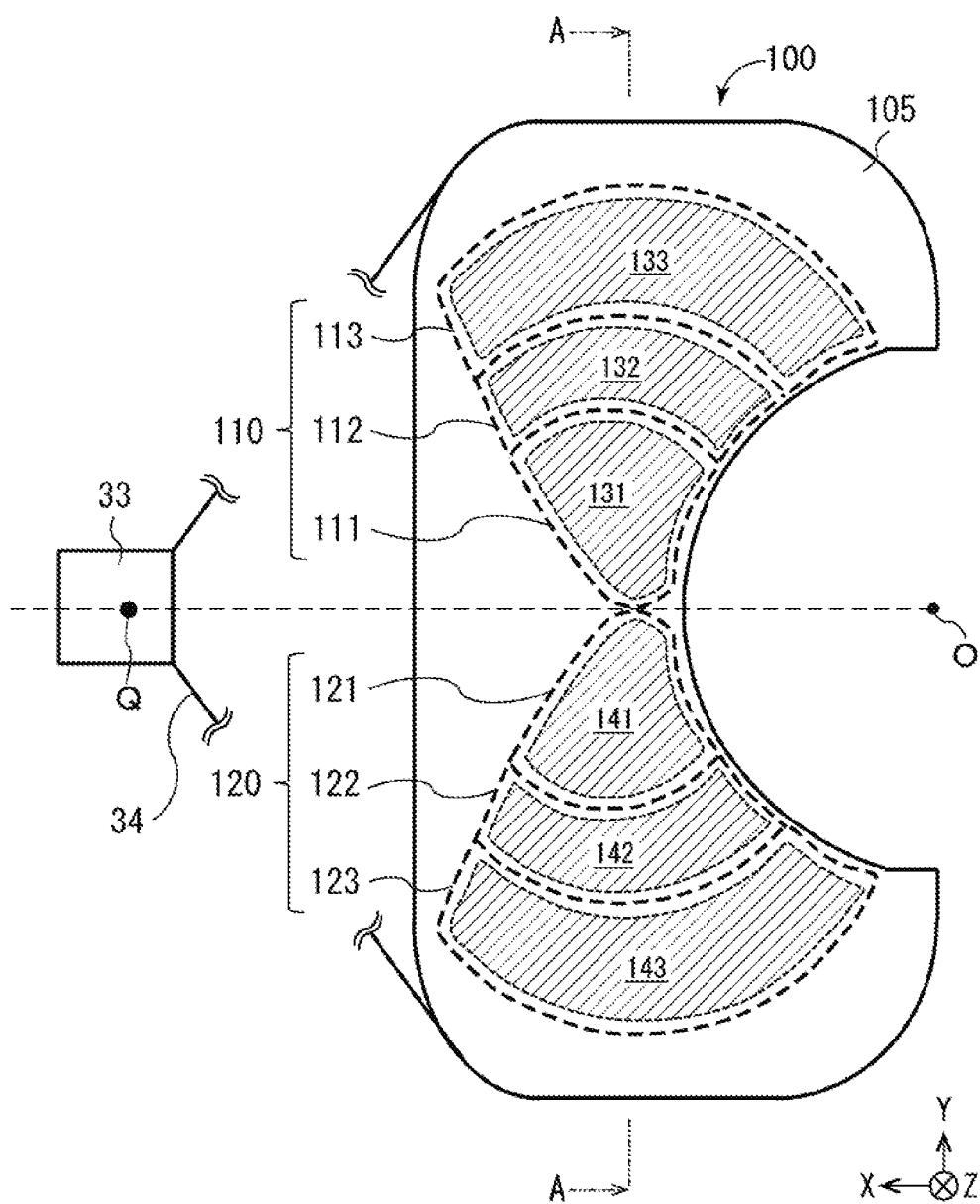
FIG. 2 is a schematic diagram of a configuration of a superconducting electromagnet apparatus.

FIG. 2 is a schematic diagram of a configuration of the superconducting electromagnet apparatus 100. In FIG. 2, the beam direction of a charged particle beam is defined as the X-axis, the direction of a magnetic field generated by the superconducting electromagnet apparatus 100 is defined as the Z-axis, and the direction orthogonal to the X-axis and the Z-axis is defined as the Y-axis. The superconducting electromagnet apparatus 100 is configured to converge a charged particle beam, which is incident from a wide range of the deflection angle φ relative to the X-axis, to the isocenter O on the XY plane.

Note that, in FIG. 2 to FIG. 10, the irradiation nozzle 40 is omitted, and for simplified illustration, the isocenter O is defined as the origin of the XYZ space, and the upstream side (accelerator side) is defined as the positive direction of the X-axis. Further, the deflection angle φ is an angle relative to the X-axis deflected at a deflection point Q of the bending magnet 33 on the XY plane.

The range of the deflection angle φ is a range larger than −90 degrees and smaller than +90 degrees, and a deflection angle range on the positive side (+Y-axis direction) and a deflection angle range on the negative side (−Y-axis direction) may be different from each other (asymmetry). For example, the positive side maximum deflection angle (φ=φ$_{MAX}$) may be any one of 10 degrees, 15 degrees, 20 degrees, 25 degrees, 30 degrees, 35 degrees, 40 degrees, 45 degrees, 50 degrees, 60 degrees, 70 degrees, 80 degrees, and 85 degrees, and the negative side maximum deflection angle (φ=−φ$_{MAX}$) may be any one of −10 degrees, −15 degrees, −20 degrees, −25 degrees, −30 degrees, −35 degrees, −40 degrees, −45 degrees, −50 degrees, −60 degrees, −70 degrees, −80 degrees, and −85 degrees.

Figure 3:
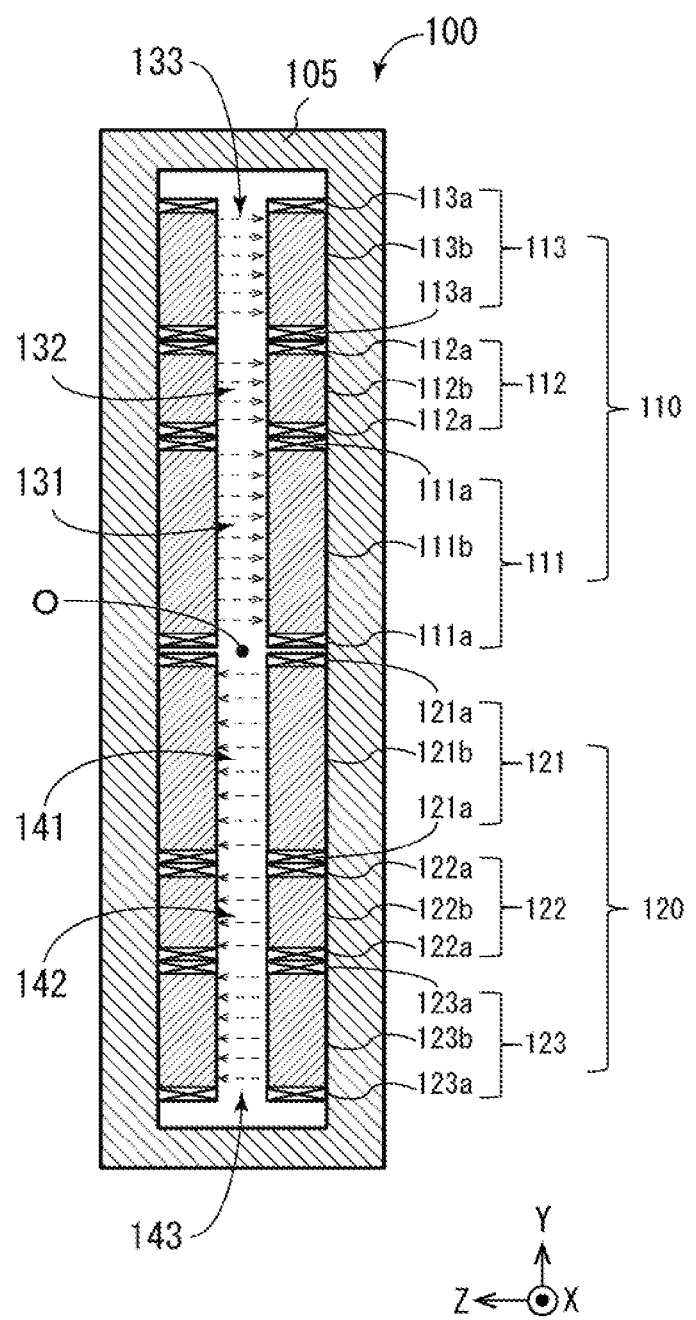
FIG. 3 is a schematic sectional view of the configuration of a superconducting electromagnet apparatus.

The superconducting electromagnet apparatus 100 has one or more sets of groups of superconducting electromagnets. As illustrated in FIG. 2 and FIG. 3, although having two sets of groups of superconducting electromagnets, namely, the group of superconducting electromagnets 110 and the group of superconducting electromagnets 120, the superconducting electromagnet apparatus 100 of the present embodiment may have any number of sets as long as it has one or more groups of superconducting electromagnets.

The group of superconducting electromagnets 110 is formed of a plurality of superconducting electromagnets 111 to 113, and the group of superconducting electromagnets 120 is formed of a plurality of superconducting electromagnets 121 to 123. In the present embodiment, although the number of superconducting electromagnets included in each group of superconducting electromagnets is three, the number is not limited thereto. To reduce the stored energy, the number of superconducting electromagnets included in each group of superconducting electromagnets may be any number as long as it is two or greater.

The superconducting electromagnets 111 to 113 generate a plurality of even magnetic fields (the effective magnetic field regions 131 to 133), respectively, which are oriented to the direction (the Z-axis direction in the drawings) orthogonal to both the beam direction of a charged particle beam and the spread direction with the deflection angle φ of the charged particle beam. The superconducting electromagnets 121 to 123 generate a plurality of even magnetic fields (the effective magnetic field regions 141 to 143), respectively, which are oriented to the direction (the Z-axis direction in the drawings) orthogonal to both the beam direction of a charged particle beam and the spread direction with the deflection angle φ of the charged particle beam. It is possible to adjust the shape and the magnetic flux density of an effective magnetic field region by adjusting the shape of a superconducting coil and a magnetic pole to adjust the flowing current.

The superconducting electromagnet 111 and the superconducting electromagnet 112 of the group of superconducting electromagnets 110 are arranged adjacent to each other, and the superconducting electromagnet 112 and the superconducting electromagnet 113 of the group of superconducting electromagnets 110 are arranged adjacent to each other. Pairs of superconducting coils 111a to 113a, which are arranged so as to interpose the path of a charged particle beam, of respective superconducting electromagnets 111 to 113 are configured to generate the effective magnetic field regions 131 to 133, respectively, in which each magnetic field is oriented to the direction (Z-axis) orthogonal to the beam direction (X-axis) of a charged particle beam. The effective magnetic field region 131 is arranged adjacent to the effective magnetic field region 132, and the effective magnetic field region 132 is arranged adjacent to the effective magnetic field region 133. The absolute value of the Y-axis position of the effective magnetic field region 132 is larger than the absolute value of the Y-axis position of the effective magnetic field region 131, and the absolute value of the Y-axis position of the effective magnetic field region 133 is larger than the absolute value of the Y-axis position of the effective magnetic field region 132.

Similarly, the superconducting electromagnet 121 and the superconducting electromagnet 122 of the group of superconducting electromagnets 120 are arranged adjacent to each other, and the superconducting electromagnet 122 and the superconducting electromagnet 123 of the group of superconducting electromagnets 120 are arranged adjacent to each other. Pairs of superconducting coils 121a to 123a, which are arranged so as to interpose the path of a charged particle beam, of respective superconducting electromagnets 121 to 123 are configured to generate the effective magnetic field regions 141 to 143, respectively, in which each magnetic field is oriented to the direction (Z-axis) orthogonal to the beam direction (X-axis) of a charged particle beam. The effective magnetic field region 141 is arranged adjacent to the effective magnetic field region 142, and the effective magnetic field region 142 is arranged adjacent to the effective magnetic field region 143. The absolute value of the Y-axis position of the effective magnetic field region 142 is larger than the absolute value of the Y-axis position of the effective magnetic field region 141, and the absolute value of the Y-axis position of the effective magnetic field region 143 is larger than the absolute value of the Y-axis position of the effective magnetic field region 142.

Note that, since the gap (the distance in the Z-axis direction) between the facing superconducting coils through which a charged particle beam passes is sufficiently smaller than the spread range of the charged particle beam on the XY plane, the spread in the Z-axis direction of the charged particle beam is not taken into consideration. Further, although there is a clearly visible gap between adjacent effective magnetic field regions for the purpose of illustration in the drawings, influence due to such a gap is small enough to be ignored in the present embodiment.

FIG. 3 is a sectional view taken along a line A-A of the superconducting electromagnet apparatus 100. The superconducting electromagnet apparatus 100 has two sets of the groups of superconducting electromagnets 110 and 120, and the groups of superconducting electromagnets 110 and 120 are formed of a plurality of superconducting electromagnets 111 to 113 and 121 to 123, respectively.

The superconducting electromagnet 111 has a pair of facing superconducting coils 111a, and a magnetic pole (pole) 111b is embedded inside the pair of superconducting coils 111a. Similarly, other superconducting electromagnets 112 to 113 and 121 to 123 have pairs of facing superconducting coils 112a to 113a and 121a to 123a, respectively, and magnetic poles (poles) 112b to 113b and 121b to 123b are embedded inside the pairs of superconducting coils 112a to 113a and 121a to 123a, respectively.

Note that, although the magnetic poles (poles) 112b to 113b and 121b to 123b are used for increasing the magnetic field intensity of the pairs of superconducting coils 112a to 113a and 121a to 123a, respectively, a form using no magnetic pole may be employed. Further, the magnetic pole is not required to be used for all the plurality of pairs of superconducting coils 112a to 113a and 121a to 123a and may be used for only the desired superconducting coil in accordance with necessity. For example, the magnetic pole may be provided or may not be provided in accordance with the radius of curvature required for circular movement of a charged particle beam in the effective magnetic field region.

A power supply (not illustrated) is connected to the superconducting electromagnet apparatus 100, and when current (excitation current) is supplied from the power supply to the superconducting electromagnets 111 to 113 and 121 to 123, the effective magnetic field regions 131 to 133 and 141 to 143 are formed.

Note that the number of superconducting electromagnets of the group of superconducting electromagnets 110 and the number of superconducting electromagnets of the group of superconducting electromagnets 120 may be different from each other. For example, the number of superconducting electromagnets of the group of superconducting electromagnets 110 in the positive (the +Y-axis direction) may be three to form the effective magnetic field regions 131 to 133, and the number of superconducting electromagnets of the group of superconducting electromagnets 120 in the negative (the −Y-axis direction) may be two to form the effective magnetic field regions 141 to 142. Further, when the range of the deflection angle $\phi$ in the positive (the +Y-axis direction) and the range of the deflection angle $\phi$ in the negative (the −Y-axis direction) are asymmetric, it is preferable to form the effective magnetic field regions to be asymmetric, accordingly. Thereby, the effective magnetic field region that is not used can be reduced, and manufacturing cost or power consumption can be reduced.

The range of the deflection angle $\phi$ of a charged particle beam deflected by the bending magnet 33 and entering the effective magnetic field regions 131 to 133 and 141 to 143 of the superconducting electromagnet apparatus 100 ranges from the positive maximum deflection angle ($\phi=\phi_{MAX}$) to the negative maximum deflection angle ($\phi=-\phi_{MAX}$), the positive maximum deflection angle $\phi_{MAX}$ is an angle that is larger than or equal to 10 degrees and smaller than 90 degrees, and the negative maximum deflection angle $-\phi_{MAX}$ is an angle that is larger than −90 degrees and smaller than or equal to −10 degrees. The deflection angle $\phi$ and the irradiation angle $\theta$ described later are angles of the path of a charged particle beam relative to the X-axis on the XY plane.

A charged particle beam incident at the positive deflection angle range ($0<\phi\leq\phi_{MAX}$) enters any one of the effective magnetic field regions 131 to 133 in accordance with the deflection angle $\phi$. The shape and the magnetic flux density B of the effective magnetic field regions 131 to 133 are set such that a charged particle beam is deflected and converged to the isocenter O when the charged particle beam enters any of the effective magnetic field regions 131 to 133. Further, similarly for the effective magnetic field regions 141 to 143, a charged particle beam incident at the negative deflection angle range ($-\phi_{MAX}\leq\phi<0$) enters any one of the effective magnetic field regions 141 to 143 in accordance with the deflection angle $\phi$. The shapes and the magnetic flux densities B of the effective magnetic field regions 141 to 143 are set such that a charged particle beam is deflected and converged to the isocenter O when the charged particle beam enters any of the effective magnetic field regions 141 to 143. The orientation of the magnetic field of the effective magnetic field regions 131 to 133 and the orientation of the magnetic field of the effective magnetic field regions 141 to 143 are opposite to each other.

The deflection angle $\phi$ of a charged particle beam entering the superconducting electromagnet apparatus 100 is controlled by the bending magnet 33. The bending magnet 33 has an electromagnet that generates a magnetic field facing the direction (the Z-axis in the drawings) orthogonal to the beam direction (the X-axis in the drawings) of a charged particle beam supplied from an accelerator (not illustrated) and deflects the passing charged particle beam and a control unit (not illustrated) that controls the intensity and the orientation of the generated magnetic field. The bending magnet 33 deflects a charged particle beam on the XY plane and launches the charged particle beam deflected at the deflection angle $\phi$ at the deflection point Q to the superconducting electromagnet apparatus 100 when the electromagnet control unit described later (not illustrated) controls the intensity and the orientation (the Z-axis direction) of the magnetic field of the bending magnet 33. Herein, the deflection point Q and the isocenter O are on the X-axis.

Calculation equations for forming respective effective magnetic field regions 131 to 133 and 141 to 143 of the superconducting electromagnet apparatus 100 will be described with reference to FIG. 4A to FIG. 4C. Note that, since deflection of a charged particle beam to the Z-axis direction is not taken into consideration, formation of respective effective magnetic field regions 131 to 133 and 141 to 143 on the XY plane will be described. Although the effective magnetic field regions 131 to 133 of the group of superconducting electromagnets 110 of the superconducting electromagnet apparatus 100 will be described, since the same applies to the effective magnetic field regions 141 to 143 of the group of superconducting electromagnets 120, the description thereof will be omitted. Note that, in the present embodiment, the gap between adjacent effective magnetic field regions is sufficiently smaller than the area of the effective magnetic field region and thus is not taken into consideration.

Figure 4A:
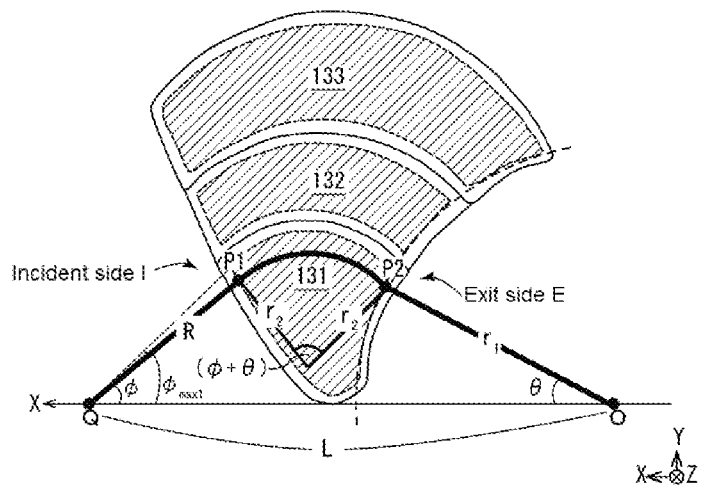
FIG. 4A to FIG. 4C are diagrams illustrating formation of an effective magnetic field region.

As illustrated in FIG. 4A, respective boundaries of the effective magnetic field regions 131 to 133 on the exit side E of a charged particle beam are determined so as to be in a range located at an equal distance $r_1$ from the isocenter O.

Respective boundaries of the effective magnetic field regions 131 to 133 on the incident side I of the charged particle beam are determined based on relational Equations (1) to (5) described later such that a charged particle beam entering, at the deflection angle $\phi$, the virtual deflection point Q located at a predetermined distance L from the isocenter O converges to the isocenter O. Herein, the virtual deflection point Q is a point under the assumption that a charged particle beam is subjected to kick of the deflection angle $\phi$ within an extremely short distance at the center of the bending magnet 33.

With respect to the shape of the effective magnetic field region 131 on the XY plane, a charged particle beam transported at the deflection angle $\phi$ enters an arbitrary (any) point P1 on the boundary of the effective magnetic field region 131 on the incident side I, travels in circular movement with a radius of curvature $r_2$ within the effective magnetic field region 131 (the central angle at this time is $(\phi+\theta)$), exits a point P2 on the boundary of the effective magnetic field region 131 on the exit side E, and is emitted to the isocenter O. That is, the point P1 and the point P2 are on an arc of a circle of the radius $r_2$ and the central angle ($\phi+\theta$). The range of the deflection angle $\phi$ of a charged particle beam entering the effective magnetic field region 131 is a range larger than 0 and smaller than or equal to $\phi_{max1}$ ($\phi_{max1} < \phi_{MAX}$).

The XY coordinate system having the isocenter O as the origin on the XY plane is considered. When the angle of a straight line connecting the point P2 on the exit side E to the isocenter O relative to the X-axis is defined as the irradiation angle $\theta$, the coordinates (x, y) of the point P1 on the incident side I, the deflection angle $\phi$, and a distance R between the point Q and the point P1 are found from the following relational Equations (1) to (4).

$$x = r_1 \cos\theta + r_2(\sin\theta + \sin\phi) \quad (1)$$

$$y = r_1 \sin\theta - r_2(\cos\theta - \cos\phi) \quad (2)$$

$$\phi = \sin^{-1}\left(\frac{r_2}{\sqrt{R^2 + r_2^2}}\right) + \sin^{-1}\left(\frac{r_1 \sin\theta - r_2 \cos\theta}{\sqrt{R^2 + r_2^2}}\right) \quad (3)$$

$$R = \sqrt{L^2 + r_1^2 - 2L(r_1\cos\theta + r_2\sin\theta)} \quad (4)$$

Herein, a magnetic field of an even magnetic flux density B occurs within the effective magnetic field region 131, and the radius of curvature $r_2$ (the radius of the circular movement) of a charged particle beam deflected in the magnetic field is expressed by Equation (5), where the momentum of a charged particle beam is denoted as p (substantially depending on an accelerator) and the charge is denoted as q.

$$r_2 = \frac{p}{qB} \quad (5)$$

It is possible to adjust the shape of the boundary of the effective magnetic field region 131 by adjusting the shape and the arrangement of the pair of superconducting coils 111a and the magnetic pole 111b of the superconducting electromagnet 111 and adjusting current flowing in the superconducting electromagnet 111 based on Equations (1) to (5) described above.

That is, the boundary is defined such that the distance between the arbitrary point P2 on the boundary of the effective magnetic field region 131 on the exit side E and the isocenter O is the equal distance $r_1$, the magnetic flux density B of the effective magnetic field region 131 is adjusted to determine $r_2$ from Equation (5), and the boundary of the effective magnetic field region 131 on the incident side I is determined such that the distance R between the point P1 on the boundary of the effective magnetic field region 131 on the incident side I and the deflection point Q has the relationship of Equation (4). Note that it is preferable that the arrangement of the deflection point Q, the superconducting electromagnet apparatus 100, and the isocenter O be adjusted in advance so that a charged particle beam passing through the deflection point Q converges to the isocenter O without being subjected to deflection by the superconducting electromagnet apparatus 100, because this can more simplify the configuration of the apparatus.

The boundary of the effective magnetic field region 131 of the superconducting electromagnet 111 of the superconducting electromagnet apparatus 100 found as described above is an ideal shape for converging a charged particle beam to the isocenter O. Note that, in the actual implementation, even when there is a shift from such an ideal shape or unevenness of a magnetic field distribution, it is possible to deflect a charged particle beam in accordance with the isocenter O by finely adjusting the excitation amount (magnetic flux density B) of the superconducting electromagnet apparatus 100 on a deflection angle $\phi$ basis in advance, storing the information thereon in a power supply apparatus (not illustrated), and controlling the deflection angle $\phi$ and the current amount of the superconducting electromagnet apparatus 100 so that the deflection angle $\phi$ and the current amount are linked. Further, when unevenness of a magnetic field distribution can be predicted in advance, it is also possible to finely adjust the orbit of a charged particle beam by adjusting the shape and the arrangement of the pair of superconducting coils 111a and the magnetic pole 111b.

The same applies to the effective magnetic field region 132 of the superconducting electromagnet 112 of the group of superconducting electromagnets 110. In the effective magnetic field region 132, however, the radius of curvature $r_3$ (the radius of circular movement) of a charged particle beam within the effective magnetic field region 132 is adjusted to converge the charged particle beam to the isocenter O by adjusting the magnetic flux density B of a generated even magnetic field (adjusting current). In the form illustrated in FIG. 4A to FIG. 4C, the radius of curvature $r_3$ is different from $r_2$, and $r_3 > r_2$ is met. Note that, for some shape of the effective magnetic field region or the like, $r_3 = r_2$ or $r_3 < r_2$ may be met.

Figure 4B:
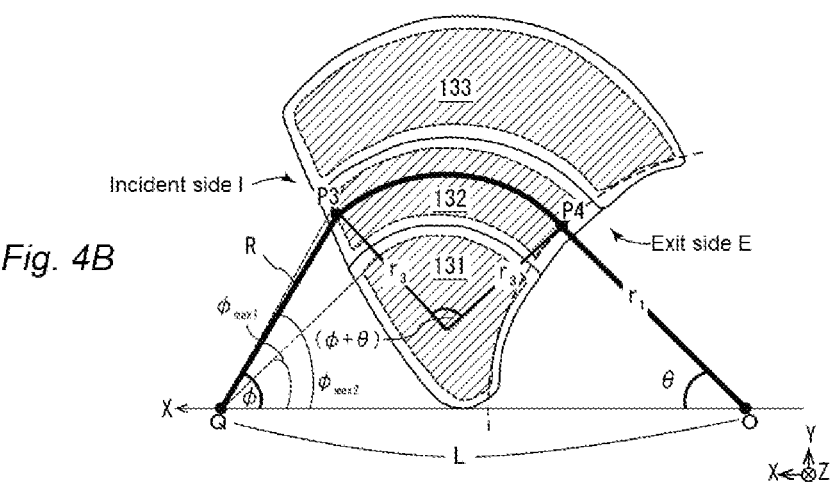

That is, as illustrated in FIG. 4B, the effective magnetic field region 132 on the XY plane is shaped such that a charged particle beam transported at the deflection angle $\phi$ enters an arbitrary (any) point P3 on the boundary of the effective magnetic field region 132 on the incident side I, travels in circular movement with a radius of curvature $r_3$ within the effective magnetic field region 132 (the central angle ($\phi+\theta$)), exits a point P4 on the boundary of the effective magnetic field region 132 on the exit side E, and is emitted to the isocenter O. That is, the point P3 and the point P4 are on an arc of a circle of the radius $r_3$ and the central angle ($\phi+\theta$). The range of the deflection angle $\phi$ of a charged particle beam entering the effective magnetic field region 132 ranges from $\phi_{max1}$ to $\phi_{max2}$ ($\phi_{max1} < \phi_{max2} < \phi_{MAX}$). When the angle of a straight line connecting the point P4 on the exit side E to the isocenter $\theta$ relative to the X-axis is defined as the irradiation angle $\theta$, the coordinates (x, y) of the point P3 on the incident side I, the deflection angle $\phi$, and the distance R between the point Q and the point P3 are found from the following relational Equations (1a) to (5a) in which "$r_2$" of Equations (1) to (5) described above is replaced with "$r_3$". The value "B" in Equation (5a) is the magnetic flux density B of the effective magnetic field region 132.

$$x = r_1 \cos\theta + r_3(\sin\theta + \sin\phi) \quad (1a)$$

$$y = r_1 \sin\theta - r_3(\cos\theta - \cos\phi) \quad (2a)$$

$$\phi = \sin^{-1}\left(\frac{r_3}{\sqrt{R^2 + r_3^2}}\right) + \sin^{-1}\left(\frac{r_1 \sin\theta - r_3 \cos\theta}{\sqrt{R^2 + r_3^2}}\right) \quad (3a)$$

-continued $$R = \sqrt{L^2 + r_1^2 - 2L(r_1\cos\theta + r_3\sin\theta)} \quad (4a)$$

$$r_3 = \frac{p}{qB} \quad (5a)$$

It is possible to adjust the shape of the boundary of the effective magnetic field region 132 by adjusting the shape and the arrangement of the pair of superconducting coils 112a and the magnetic pole 112b of the superconducting electromagnet 112 and adjusting current flowing in the superconducting electromagnet 112 based on Equations (1a) to (5a) described above. That is, the boundary is defined such that the distance between the arbitrary point P4 on the boundary of the effective magnetic field region 132 on the exit side E and the isocenter O is the equal distance $r_1$, the magnetic flux density B of the effective magnetic field region 132 is adjusted to determine $r_3$ from Equation (5a), and the boundary of the effective magnetic field region 132 on the incident side I is determined such that the distance R between the point P3 on the boundary of the effective magnetic field region 132 on the incident side I and the deflection point Q has the relationship of Equation (4a).

The same applies to the effective magnetic field region 133 of the superconducting electromagnet 113 of the group of superconducting electromagnets 110. In the effective magnetic field region 133, however, the magnetic flux density B of a generated even magnetic field is adjusted (current is adjusted), and thereby, the radius of curvature $r_4$ (the radius of circular movement) of a charged particle beam within the effective magnetic field region 133 is adjusted to converge the charged particle beam to the isocenter O. In the form illustrated in FIG. 4A to FIG. 4C, the radius of curvature $r_4$ is different from $r_2$ or $r_3$, and $r_4 > r_3 > r_2$ is met. Note that, for some shape of the effective magnetic field region, $r_4 = r_3 = r_2$, or $r_4 < r_3 < r_2$, may be met.

Figure 4C:
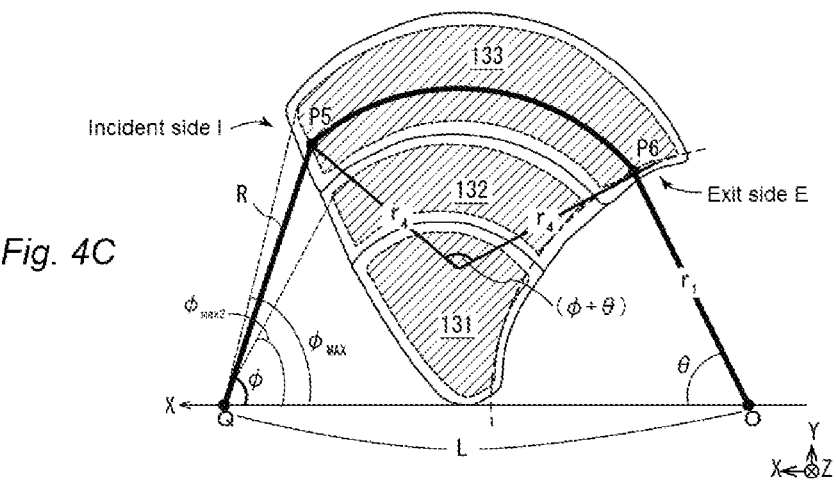

That is, as illustrated in FIG. 4C, the effective magnetic field region 133 on the XY plane is shaped such that a charged particle beam transported at the deflection angle $\phi$ enters an arbitrary (any) point P5 on the boundary of the effective magnetic field region 133 on the incident side I, travels in circular movement with a radius of curvature $r_4$ within the effective magnetic field region 133 (the central angle ($\phi+\theta$)), exits a point P6 on the boundary of the effective magnetic field region 133 on the exit side E, and is emitted to the isocenter O. That is, the point P5 and the point P6 are on an arc of a circle of the radius $r_4$ and the central angle ($\phi+\theta$). The range of the deflection angle $\phi$ of a charged particle beam entering the effective magnetic field region 133 ranges from $\phi_{max2}$ to $\phi_{MAX}$. When the angle of a straight line connecting the point P6 on the exit side E to the isocenter O relative to the X-axis is defined as the irradiation angle $\theta$, the coordinates (x, y) of the point P5 on the incident side I, the deflection angle $\phi$, and the distance R between the point Q and the point P5 are found from the following relational Equations (1b) to (5b) in which "$r_2$" of Equations (1) to (5) described above is replaced with "$r_4$". The value "B" in Equation (5b) is the magnetic flux density B of the effective magnetic field region 133.

$$x = r_1\cos\theta + r_4(\sin\theta + \sin\phi) \quad (1b)$$

$$y = r_1\sin\theta - r_4(\cos\theta - \cos\phi) \quad (2b)$$

-continued $$\phi = \sin^{-1}\left(\frac{r_4}{\sqrt{R^2 + r_4^2}}\right) + \sin^{-1}\left(\frac{r_1\sin\theta - r_4\cos\theta}{\sqrt{R^2 + r_4^2}}\right) \quad (3b)$$

$$R = \sqrt{L^2 + r_1^2 - 2L(r_1\cos\theta + r_4\sin\theta)} \quad (4b)$$

$$r_4 = \frac{p}{qB} \quad (5b)$$

It is possible to adjust the shape of the boundary of the effective magnetic field region 133 by adjusting the shape and the arrangement of the pair of superconducting coils 113a and the magnetic pole 113b of the superconducting electromagnet 113 and adjusting current flowing in the superconducting electromagnet 113 based on Equations (1b) to (5b) described above. That is, the boundary is defined such that the distance between the arbitrary point P6 on the boundary of the effective magnetic field region 133 on the exit side E and the isocenter O is the equal distance $r_1$, the magnetic flux density B of the effective magnetic field region 133 is adjusted to determine $r_4$ from Equation (5b), and the boundary of the effective magnetic field region 133 on the incident side I is determined such that the distance R between the point P5 on the boundary of the effective magnetic field region 133 on the incident side I and the deflection point Q has the relationship of Equation (4b).

The same as the effective magnetic field regions 131 to 133 applies for the shape on the XY plane of the effective magnetic field regions 141 to 143 of the superconducting electromagnets 121 to 123 of the group of superconducting electromagnets 120, and the description thereof will be omitted.

As described above, it is possible to converge the charged particle beam to the isocenter O at an irradiation angle of the irradiation angle $\theta$ in accordance with the deflection angle $\phi$ by defining the shapes of the effective magnetic field regions 131 to 133 of the superconducting electromagnets 111 to 113 on the XY plane.

Figure 11:
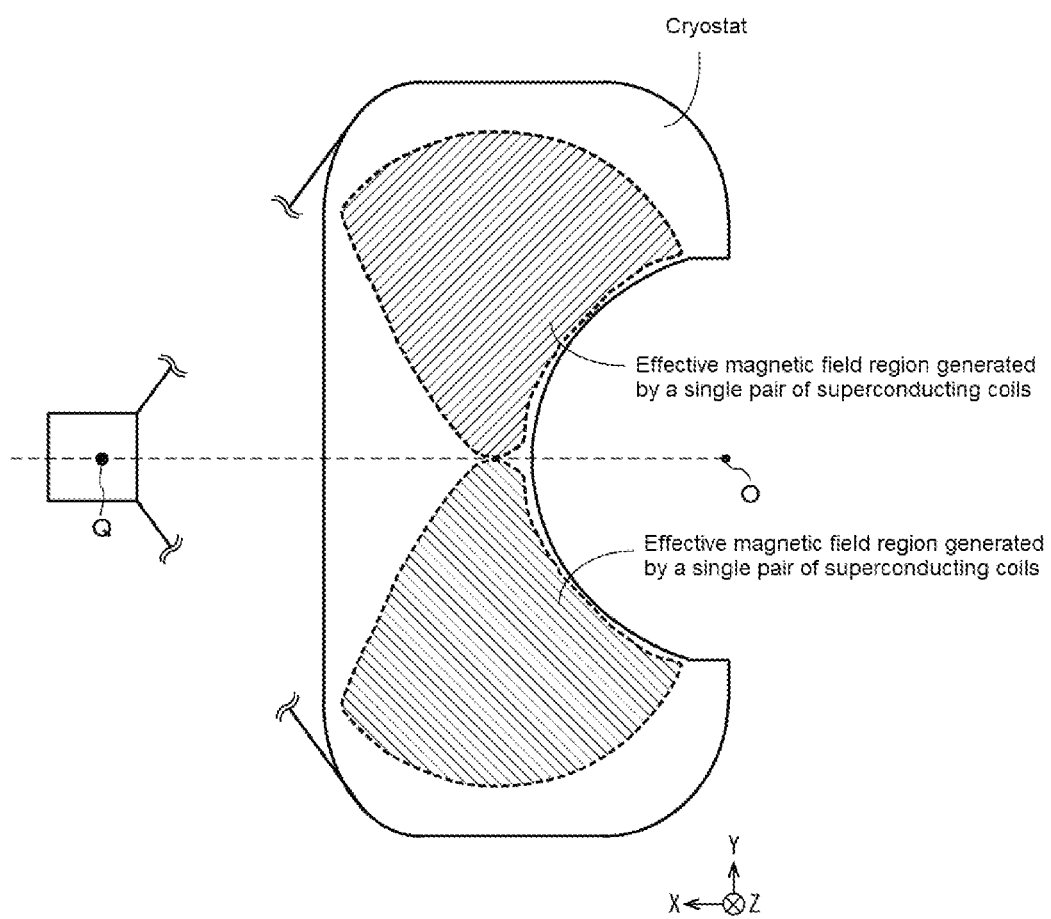
FIG. 11 is a diagram illustrating a superconducting electromagnet apparatus of the conventional art.

Further, as compared to a case where the effective magnetic field region that causes a charged particle beam to converge to the isocenter O as with the conventional art illustrated in FIG. 11 is formed by using a single superconducting electromagnet, the stored energy can be reduced when the groups of superconducting electromagnets 110 and 120 according to the present embodiment are used. That is, since the stored energy of a superconducting coil ($=LI^2/2$) is proportional to the inductance L of the superconducting coil (L=BS/I, and S denotes the area where the magnetic flux crosses, i.e. the area of the effective magnetic field region on the XY plane), the area S of the superconducting electromagnets 111 to 113 and the area S of the superconducting electromagnets 121 to 123 can be reduced as compared to the areas of a conventional single superconducting electromagnet. Thus, the stored energy of each of the superconducting electromagnets 111 to 113 and 121 to 123 can be reduced as compared to that of a conventional single superconducting electromagnet. As a result, the voltage between terminals of the superconducting coil or the quench voltage generated during quenching can be reduced, and a leakage magnetic field generated from the superconducting coil can also be reduced.

Second Embodiment

The second embodiment of the present invention relates to a configuration in which each of the superconducting electromagnets 111 to 113 of the group of superconducting electromagnets 110 is arranged inclined with respect to an adjacent superconducting coil on the XY plane. Note that the inclination in the Z-axis direction is not taken into consideration. Further, since the same applies to the group of superconducting electromagnets 120, the description thereof will be omitted.

Figure 5A:
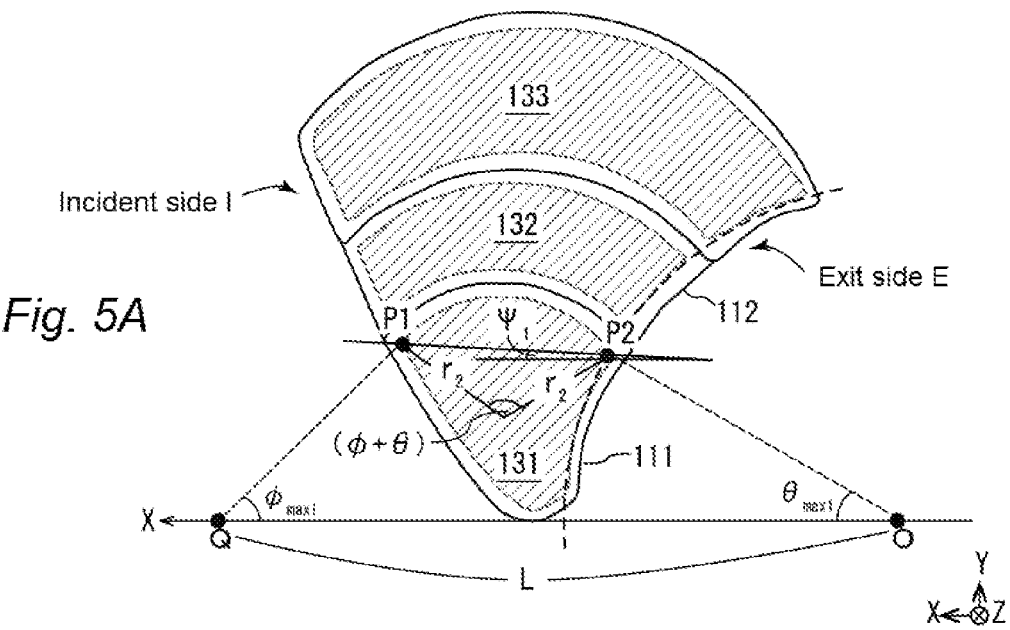
FIG. 5A and FIG. 5B are diagrams illustrating inclined arrangement of superconducting electromagnets.

As illustrated in FIG. 5A, on the XY plane, the superconducting electromagnet 112 forming the effective magnetic field region 132 is arranged inclined at an angle $\psi$ with respect to the X-axis in accordance with the shape of the effective magnetic field region 131 of the adjacent superconducting electromagnet 111. That is, the effective magnetic field region 132 is inclined at the angle $\psi$ with respect to the effective magnetic field region 131 and arranged adjacent to the effective magnetic field region 131.

For example, in the effective magnetic field region 131, the straight line passing through the incident point P1 and the exit point P2 located at positions closest to the effective magnetic field region 132 side (a straight line connecting the incident point P1 to the exit point P2 on the path through which a charged particle beam entering the effective magnetic field region 131 at the deflection angle $\phi=\phi_{max1}$ passes) is inclined at an angle $\psi_1$ with respect to the X-axis. The angle $\psi_1$ satisfies $\psi_1=(\theta-\phi)/2=(\theta_{max1}-\phi_{max1})/2$ ($\theta$ at $\phi=\phi_{max1}$ is denoted as $\theta_{max1}$). In such a way, on the XY plane, the superconducting electromagnet 112 is inclined at the angle $\psi_1$ relative to the X-axis and arranged adjacent to the superconducting electromagnet 111. That is, the effective magnetic field region 132 is inclined at the angle $\psi_1$ with respect to the effective magnetic field region 131 and arranged adjacent to the effective magnetic field region 131.

Figure 5B:
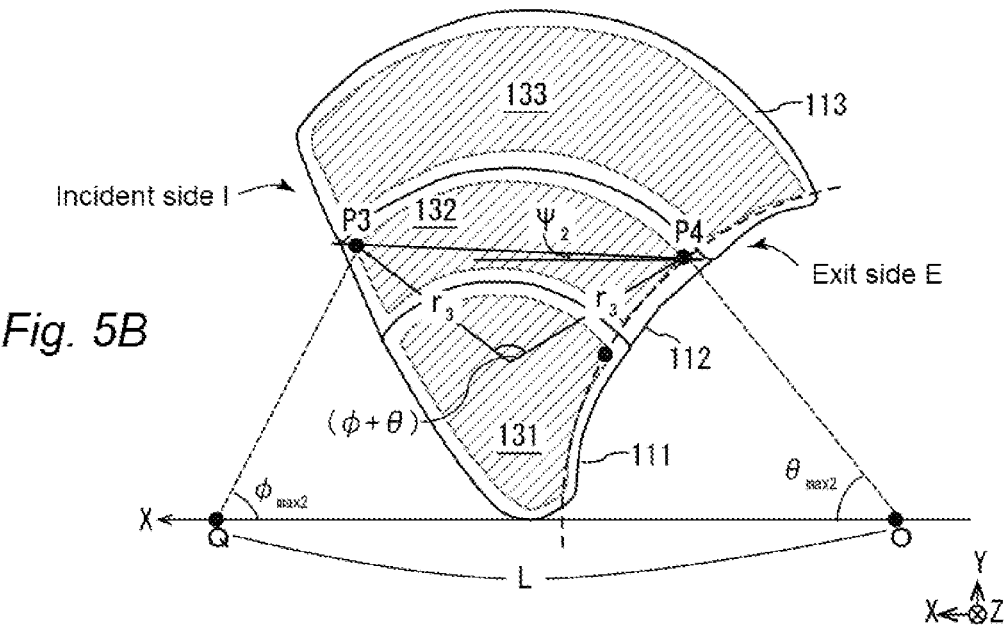

Similarly, as illustrated in FIG. 5B, on the XY plane, the superconducting electromagnet 113 forming the effective magnetic field region 133 is arranged inclined at an angle $\psi$ relative to the X-axis in accordance with the shape of the effective magnetic field region 132 of the adjacent superconducting electromagnet 112. That is, in the effective magnetic field region 132, the straight line passing through the incident point P3 and the exit point P4 located at positions closest to the effective magnetic field region 133 side (a straight line connecting the incident point P3 to the exit point P4 on the path through which a charged particle beam entering the effective magnetic field region 132 at the deflection angle $\phi=\phi_{max2}$ passes) is inclined at an angle $\psi_2$ with respect to the X-axis. The angle $\psi_2$ is expressed by $\psi_2=(\theta-\phi)/2=(\theta_{max2}-\phi_{max2})/2$ ($\theta$ at $\phi=\phi_{max2}$ is denoted as $\theta_{max2}$). In such a way, on the XY plane, the superconducting electromagnet 113 is inclined at the angle $\psi_2$ relative to the X-axis and arranged adjacent to the superconducting electromagnet 112. That is, the effective magnetic field region 133 is inclined at the angle $\psi_2$ with respect to the effective magnetic field region 132 and arranged adjacent to the effective magnetic field region 132.

It is possible to connect adjacent effective magnetic field regions to each other in a seamless manner by arranging each of the superconducting electromagnets 111 to 113 and 121 to 123 so as to be inclined at the angle iv relative to the X-axis with respect to adjacent superconducting electromagnet on the XY plane. Note that, for the purpose of illustration, although there is a visible gap between adjacent effective magnetic field regions for the purpose of illustration on the drawings, influence due to such a gap is small enough to ignore in the present embodiment.

Third Embodiment

Figure 6:
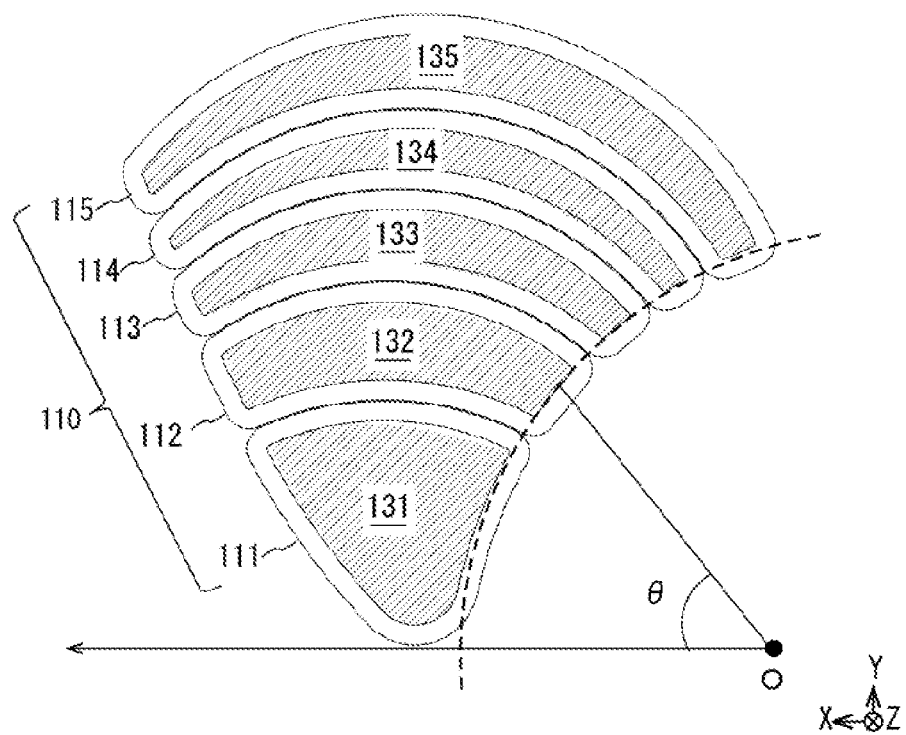
FIG. 6 is a diagram illustrating superconducting electromagnets having the same inductance.

The third embodiment of the present invention relates to a form in which the number of superconducting electromagnets 111 to 115 included in the group of superconducting electromagnets 110 included in the cryostat 105 is five and respective inductances L of the superconducting electromagnets 111 to 115 are the same (FIG. 6). Note that the same applies to the group of superconducting electromagnets 120, and the description thereof will be omitted. Further, the number of superconducting electromagnets is not limited to five in the present embodiment. Further, although the areas of the effective magnetic field regions 131 to 135 may seem to be unequal in a strict sense in FIG. 6, such inequality is not intended.

In the present embodiment, the plurality of superconducting electromagnets 111 to 115 have the effective magnetic field regions 131 to 135 having the area equal to each other on the XY plane, respectively. Further, respective magnetic flux densities B of the effective magnetic field regions 131 to 135 are set equal to each other. Accordingly, respective inductances L of the superconducting electromagnets 111 to 115 of the group of superconducting electromagnets 110 are equal to each other. Further, the present embodiment is configured such that charged particle beams travel in circular movement with the same radius of curvature inside respective effective magnetic field regions 131 to 135 and converge to the isocenter O.

With the same inductances L of the superconducting electromagnets 111 to 115, the impedances from power supply connected to the superconducting electromagnets 111 to 115 are substantially the same, adjustment of the power supply for each of the superconducting electromagnets 111 to 115 is unnecessary, and the number of power supply can be reduced. The present embodiment can be configured such that a single power supply 150 and a single switching device 151 are used to supply current to each of the superconducting electromagnets 111 to 115.

Figure 7:
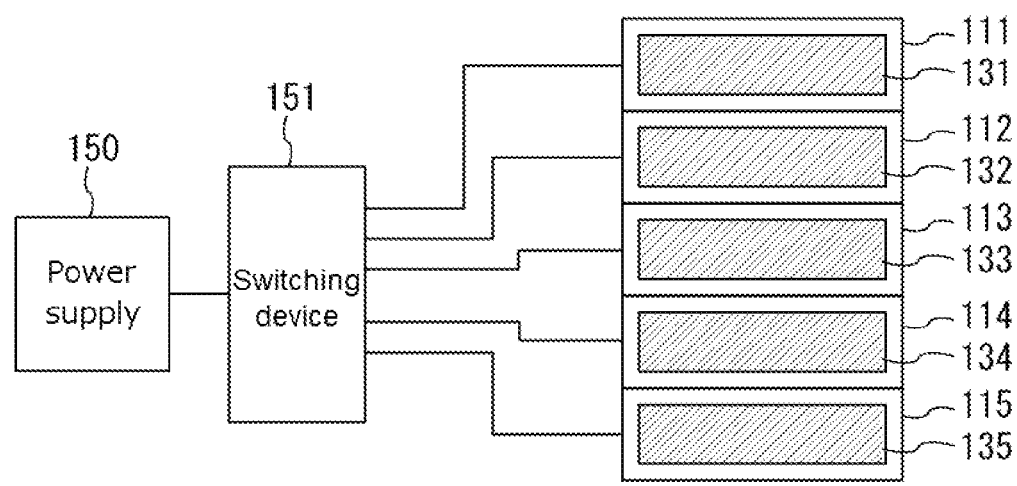
FIG. 7 is a block diagram of a power supply, a switching device, and superconducting electromagnets.
Figure 8:
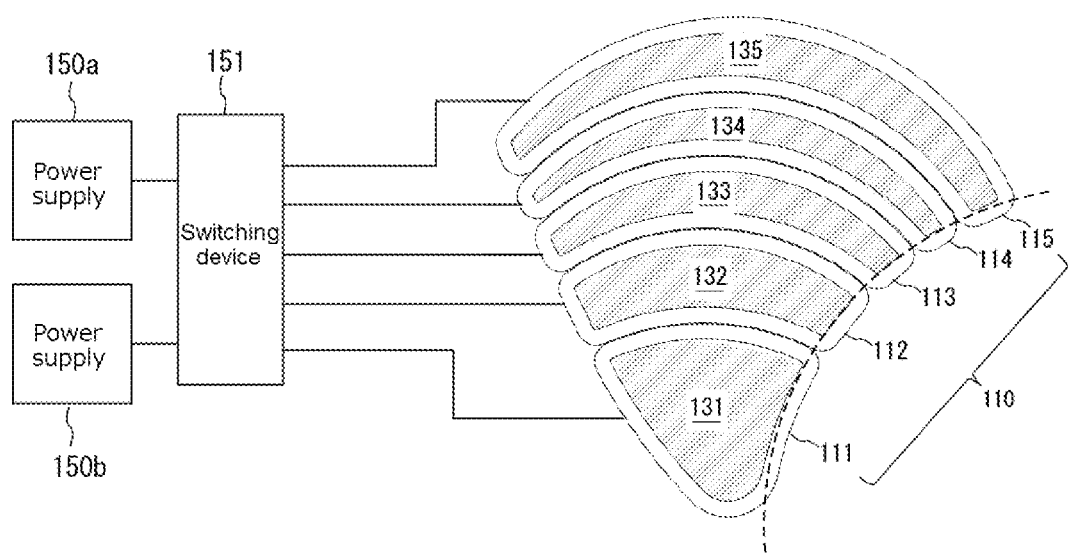
FIG. 8 is a block diagram of power supply, a switching device, and superconducting electromagnets.

FIG. 7 is a block diagram of the power supply 150, the switching device 151, the superconducting electromagnets 111 to 115, and the effective magnetic field regions 131 to 135.

Some of the superconducting electromagnets 111 to 115 to be used is selected in accordance with the irradiation angle $\theta$ to the isocenter O, supply of current from the power supply 150 is switched by the switching device 151, and thereby, current can be effectively supplied to the effective magnetic field regions 131 to 135 through which a charged particle beam passes. For example, when a charged particle beam enters the effective magnetic field region 132, the current from the power supply 150 may be switched by the switching device 151 to excite only the superconducting electromagnet 112 that generates the effective magnetic field region 132 and not to excite the remaining superconducting electromagnets 111 and 113 to 115. Further, for example, when a charged particle beam enters the effective magnetic field region 134, the current from the power supply 150 may be switched by the switching device 151 to excite only the superconducting electromagnet 114 that generates the effective magnetic field region 134 and not to excite the remaining superconducting electromagnets 111 to 113 and 115. By selectively exciting a superconducting electromagnet in such a way, it is possible to suppress occurrence of an unnecessary magnetic field, reduce energy consumption, and reduce occurrence of quenching or a leakage magnetic field.

In the present embodiment, by setting the same magnetic flux densities B of effective magnetic field regions and the same areas S of the effective magnetic field regions on the XY plane for respective superconducting electromagnets included in a group of superconducting electromagnets to have the even inductance L, it is possible to reduce the number of power supply of the superconducting electromagnets or the number of superconducting electromagnets to be excited, and this enables easier power supply management.

Fourth Embodiment

In the fourth embodiment of the present invention, two power supply for exciting superconducting electromagnets are used (FIG. 8) in the same manner as in the third embodiment. The present embodiment relates to a configuration in which a charged particle beam passes through adjacent two effective magnetic field regions and converges to the isocenter O.

While respective inductances L of the superconducting electromagnets 111 to 115 included in the group of superconducting electromagnets 110 are the same in the same manner as in the third embodiment, the present embodiment is configured such that the magnetic flux densities B of respective effective magnetic field regions 131 to 135 are different from each other and the areas of the effective magnetic field regions 131 to 135 on the XY plane are different from each other in order to converge a charged particle beam to the isocenter O.

That is, in the present embodiment, when respective current values I are even for the superconducting electromagnets 111 to 115, $L=B1*S1=B2*S2=B3*S3=B4*S4=B5*S5$ is satisfied, where the magnetic flux densities of the effective magnetic field regions 131 to 135 are denoted as B1 to B5, respectively, and the areas on the XY plane thereof are denoted as S1 to S5, respectively. The areas S1 to S5 of the effective magnetic field regions 131 to 135 are determined so as to satisfy the above relationship. Since the inductances of superconducting electromagnets 111 to 115 are equal to each other, the impedances from the power supply are also the same. As a result, adjustment of the power supply for each of the superconducting electromagnets 111 to 115 is unnecessary, and this enables easier power supply management.

When a charged particle beam enters the effective magnetic field region 133 after entering the effective magnetic field region 132 and then returns to the effective magnetic field region 132 to irradiate the isocenter O, the power supply 150*a* excites the superconducting electromagnet 112, and a power supply 150*b* excites the superconducting electromagnet 113. Since the remaining superconducting electromagnets 111, 114, and 115 are not excited, influence of a leakage magnetic field can be reduced.

Table 1 illustrates Examples I to V of excitation patterns of the superconducting electromagnets 111 to 115, which are patterns according to which supply of current is switched by the switching device 151 in accordance with the irradiation angle θ to the isocenter O.

TABLE 1

| Excitation pattern | Superconducting electromagnet 115 | Superconducting electromagnet 114 | Superconducting electromagnet 113 | Superconducting electromagnet 112 | Superconducting electromagnet 111 |
|---|---|---|---|---|---|
| I | Power supply 150a | Power supply 150b | | | |
| II | | Power supply 150b | Power supply 150a | | |
| III | | | Power supply 150a | Power supply 150b | |
| IV | | | | Power supply 150b | Power supply 150a |
| V | | | | | Power supply 150a |

The excitation pattern I corresponds to a case where a charged particle beam passes through the effective magnetic field region 134 of the superconducting electromagnet 114 and/or the effective magnetic field region 135 of the superconducting electromagnet 115 (that is, in accordance with the irradiation angle θ at which a charged particle beam passes through the effective magnetic field regions 134 and/or 135), and in accordance with the operation of the switching device 151, the superconducting electromagnets 114 and 115 are excited by the power supply 150*a* and the power supply 150*b*, respectively, and the remaining superconducting electromagnets 111 to 113 are not excited.

The excitation pattern II corresponds to a case where a charged particle beam passes through the effective magnetic field region 133 of the superconducting electromagnet 113 and/or the effective magnetic field region 134 of the superconducting electromagnet 114 (that is, in accordance with the irradiation angle θ at which a charged particle beam passes through the effective magnetic field regions 133 and/or 134), the superconducting electromagnets 113 and 114 are excited by the power supply 150*b* and the power supply 150*a*, respectively, and the remaining superconducting electromagnets 111, 112, and 115 are not excited.

The excitation pattern III corresponds to a case where a charged particle beam passes through the effective magnetic field region 132 of the superconducting electromagnet 112 and/or the effective magnetic field region 133 of the superconducting electromagnet 113 (that is, in accordance with the irradiation angle θ at which a charged particle beam passes through the effective magnetic field regions 132 and/or 133), the superconducting electromagnets 112 and 113 are excited by the power supply 150a and the power supply 150b, respectively, and the remaining superconducting electromagnets 111, 114, and 115 are not excited.

The excitation pattern IV corresponds to a case where a charged particle beam passes through the effective magnetic field region 131 of the superconducting electromagnet 111 and/or the effective magnetic field region 132 of the superconducting electromagnet 112 (that is, in accordance with the irradiation angle θ at which a charged particle beam passes through the effective magnetic field regions 131 and/or 132), the superconducting electromagnets 111 and 112 are excited by the power supply 150b and the power supply 150a, respectively, and the remaining superconducting electromagnets 113 to 115 are not excited.

The excitation pattern V corresponds to a case where a charged particle beam passes through only the effective magnetic field region 131 of the superconducting electromagnet 111 (that is, in accordance with the irradiation angle θ at which a charged particle beam passes through the effective magnetic field region 131), the superconducting electromagnet 111 is excited by the power supply 150a, and the remaining superconducting electromagnets 112 to 115 are not excited.

As described above, in the present embodiment, by selectively exciting the superconducting electromagnet, it is possible to suppress occurrence of an unnecessary magnetic field, reduce energy consumption, and reduce occurrence of quenching or a leakage magnetic field. Further, with design such that the inductances of respective superconducting electromagnets included in a group of superconducting electromagnets are equal to each other, it is possible to simplify the power supply for superconducting electromagnets, and reduce the number of power supply to be used and the number of superconducting coils to be excited, and this enables easier power supply management.

Fifth Embodiment

The fifth embodiment of the present invention relates to a configuration to cope with a case where the gap between adjacent effective magnetic field regions of the effective magnetic field regions 131 to 133 generated by the three superconducting electromagnets 111 to 113 included in the group of superconducting electromagnets 110 is relatively large and this causes influence of a reduction in the magnetic field intensity between the adjacent effective magnetic field regions. Note that the number of superconducting electromagnets of the group of superconducting electromagnets 110 is not limited to three.

Figure 9A:
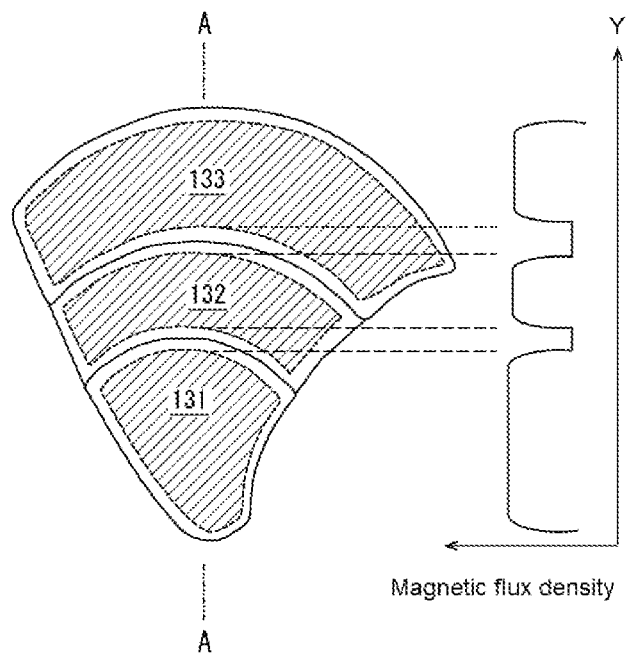
FIG. 9A and FIG. 9B are diagrams illustrating a relationship between magnetic flux densities and effective magnetic field regions.
Figure 9B:
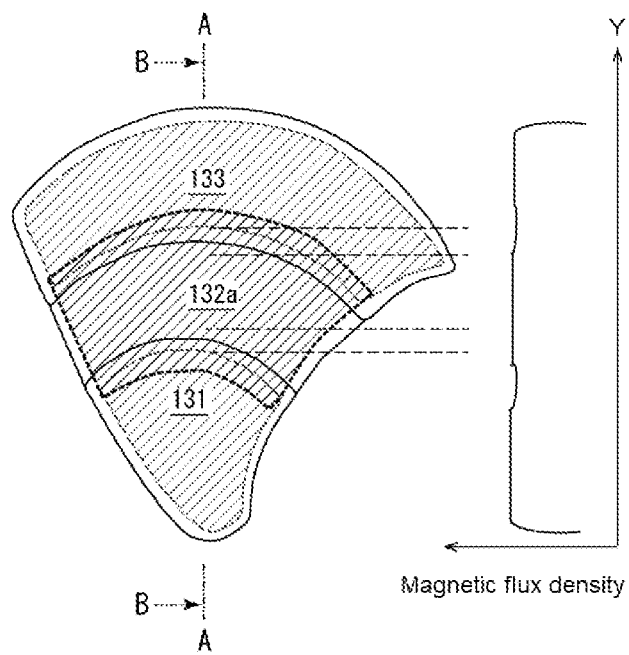

FIG. 9A and FIG. 9B are diagrams illustrating the relationship between the effective magnetic field regions 131 to 133 and the magnetic flux density B (on the line A-A) of the superconducting electromagnets 111 to 113. FIG. 9A illustrates a state where the gap between the adjacent effective magnetic field regions 131 and 132 and the gap between the adjacent effective magnetic field regions 132 and 133 are relatively large and the magnetic flux density B is relatively low in the gaps.

In the present embodiment, as illustrated in FIG. 9B, the shape and the arrangement of the superconducting electromagnet 112 are adjusted such that an effective magnetic field region 133a of the superconducting electromagnet 112 partially overlaps the adjacent effective magnetic field regions 131 and 133. Note that, although omitted in FIG. 9A and FIG. 9B, the group of superconducting electromagnets 120 is the same as the group of superconducting electromagnets 110.

Figure 10:
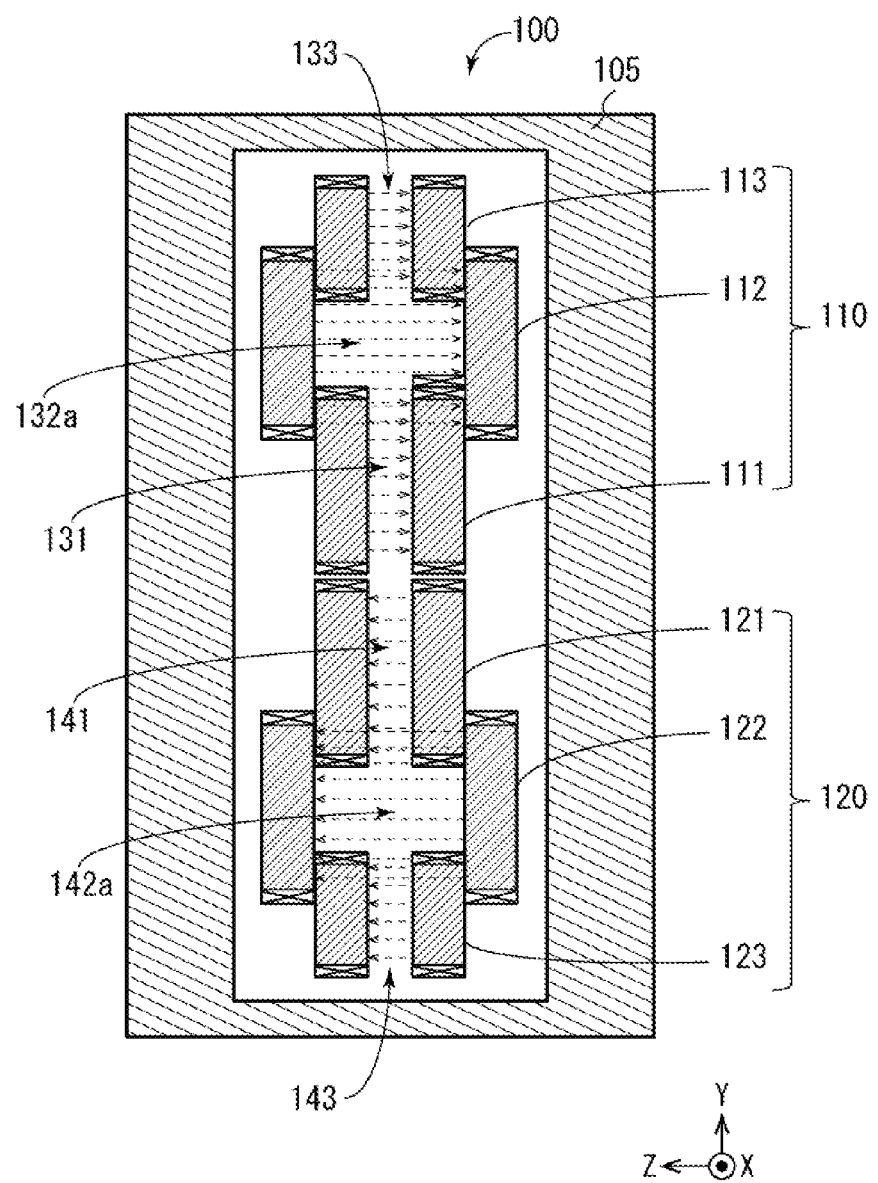
FIG. 10 is a schematic sectional view of a configuration of a superconducting electromagnet apparatus.

FIG. 10 is a sectional view taken along a line B-B of FIG. 9B. As illustrated in FIG. 10, the superconducting electromagnet 112 is arranged shifted in the Z direction with respect to the superconducting electromagnets 111 and 113, and an effective magnetic field region 132a partially overlaps the adjacent effective magnetic field regions 131 and 133. Similarly, the superconducting electromagnet 122 is arranged shifted in the Z direction with respect to the superconducting electromagnets 121 and 123, and an effective magnetic field region 142a partially overlaps the adjacent effective magnetic field regions 141 and 143.

With the configuration according to the present embodiment, the problem of a reduction in the magnetic field intensity between adjacent effective magnetic field regions is eliminated or reduced.

With the superconducting electromagnet apparatus according to one embodiment of the present invention, irradiation of a charged particle beam is enabled at a continuous irradiation angle θ with respect to the isocenter, stored energy of the superconducting electromagnet can be reduced compared to the conventional superconducting electromagnet apparatus using a single superconducting electromagnet, and as a result, influence of a quench voltage and a leakage magnetic field can also be reduced.

The size, the material, the shape, the relative position of components, or the like described above may be changed in accordance with the structure of the apparatus to which the present invention is applied or various conditions. It is not intended to limit the disclosure to any specific terms used in the description and the embodiments, those skilled in the art can use another equivalent component, and the embodiments described above can be modified and changed differently as long as not departing from the spirit or the scope of the present invention. Further, even if not explicitly described, the feature described in association with one of the embodiments of the present invention can be used together with another embodiment.

The present application is based on and claims priority from Japanese Patent Application No. 2020-63275, filed Mar. 31, 2020, the disclosure of which is hereby incorporated by reference herein in its entirety.

LIST OF REFERENCE SYMBOLS 10 charged particle irradiation apparatus
20 accelerator
30 charged particle beam transport system
31 charged particle beam adjustment unit
32 vacuum chamber
33 bending magnet
34 sector-shaped vacuum chamber
100 superconducting electromagnet apparatus
105 cryostat
111 to 115, 121 to 125 superconducting electromagnet
111a to 113a, 121a to 123a superconducting coil
111b to 113b, 121b to 123b magnetic pole
131 to 133, 141 to 143 effective magnetic field region
150, 150a, 150b power supply
151 switching device

What is claimed is:

1. A superconducting electromagnet apparatus comprising a group of superconducting electromagnets including a first superconducting electromagnet and a second superconducting electromagnet arranged adjacent to the first superconducting electromagnet, wherein a pair of superconducting coils of the first superconducting electromagnet, the pair being arranged so as to interpose a path of a charged particle beam, is configured to generate a first effective magnetic field region whose magnetic field faces a direction (Z-axis) orthogonal to a beam direction (X-axis) of a charged particle beam, and an axis orthogonal to both the X-axis and the Z-axis is defined as a Y-axis, wherein a pair of superconducting coils of the second superconducting electromagnet, the pair being arranged so as to interpose a path of a charged particle beam, is configured to generate a second effective magnetic field region whose magnetic field faces the direction (Z-axis) orthogonal to the beam direction (X-axis) of a charged particle beam, wherein an orientation of a magnetic field of the first superconducting electromagnet and an orientation of a magnetic field of the second superconducting electromagnet are the same, wherein the first effective magnetic field region and the second effective magnetic field region are arranged adjacent to each other, and the absolute value of a Y-axis position of the second effective magnetic field region is larger than the absolute value of a Y-axis position of the first effective magnetic field region, (i) wherein for the first effective magnetic field region, on an XY plane, a charged particle beam deflected at a deflection angle $\phi$ relative to the X-axis at a deflection point Q and entering the first effective magnetic field region is deflected by the first effective magnetic field region and irradiates an isocenter at an irradiation angle $\theta$ relative to the X-axis, an arbitrary point P2 on a boundary defining the first effective magnetic field region and located on an exit side of a charged particle beam is positioned at an equal distance $r_1$ from the isocenter, the point P2 and a point P1 on a boundary defining the first effective magnetic field region and located on an incident side of a charged particle beam are on an arc of a circle of a radius $r_2$ and a central angle ($\theta+\phi$), and a distance R between the deflection point Q and the point P1 satisfies relational Equation (4), where a distance between the deflection point Q and the isocenter is denoted as L:

$$R = \sqrt{L^2 + r_1^2 - 2L(r_1\cos\theta + r_2\sin\theta)}, \quad (4)$$

and (ii) wherein for the second effective magnetic field region, on the XY plane, a charged particle beam deflected at a deflection angle $\phi$ relative to the X-axis at a deflection point Q and entering the second effective magnetic field region is deflected by the second effective magnetic field region and irradiates the isocenter at an irradiation angle $\theta$ relative to the X-axis, an arbitrary point P4 on a boundary defining the second effective magnetic field region and located on an exit side of a charged particle beam is positioned at the equal distance $r_1$ from the isocenter, the point P4 and a point P3 on a boundary defining the second effective magnetic field region and located on an incident side of a charged particle beam are on an arc of a circle of a radius $r_3$ and a central angle ($\theta+\phi$), and a distance R between the deflection point Q and the point P3 satisfies relational Equation (4a):

$$R = \sqrt{L^2 + r_1^2 - 2L(r_1\cos\theta + r_3\sin\theta)}. \quad (4a)$$

2. The superconducting electromagnet apparatus according to claim 1, wherein when a deflection angle $\phi$ determined by the point P1 and the deflection point Q, the point P1 being included in the first effective magnetic field region and located at a position closest to the second effective magnetic field region side, is denoted as $\phi_{max}$, and an irradiation angle $\theta$ of a charged particle beam, which enters the first effective magnetic field region at the deflection angle $\phi_{max}$, to the isocenter is denoted as $\theta_{max}$, on the XY plane, the second effective magnetic field region is inclined, with respect to the first effective magnetic field region, at an angle $\psi=(\theta_{max}-\phi_{max})/2$ relative to the X-axis and arranged adjacent to the first effective magnetic field region.

3. The superconducting electromagnet apparatus according to claim 1, wherein an inductance of the first superconducting electromagnet and an inductance of the second superconducting electromagnet are the same.

4. The superconducting electromagnet apparatus according to claim 1, wherein a magnetic pole is embedded inside a superconducting coil of the first superconducting electromagnet or inside a superconducting coil of the second superconducting electromagnet.

5. The superconducting electromagnet apparatus according to claim 1, wherein the second effective magnetic field region partially overlaps the first effective magnetic field region.

6. The superconducting electromagnet apparatus according to claim 1, wherein the group of superconducting electromagnets further comprises a third superconducting electromagnet arranged adjacent to the second superconducting electromagnet, wherein a pair of superconducting coils of the third superconducting electromagnet, the pair being arranged so as to interpose a path of a charged particle beam, is configured to generate a third effective magnetic field region whose magnetic field faces the direction (Z-axis) orthogonal to the beam direction (X-axis) of a charged particle beam, wherein an orientation of a magnetic field of the second superconducting electromagnet and an orientation of a magnetic field of the third superconducting electromagnet are the same, wherein the second effective magnetic field region and the third effective magnetic field region are arranged adjacent to each other, and the absolute value of a Y-axis position of the third effective magnetic field region is larger than the absolute value of a Y-axis position of the second effective magnetic field region, (iii) wherein for the third effective magnetic field region, on the XY plane, a charged particle beam deflected at a deflection angle φ relative to the X-axis at a deflection point Q and entering the third effective magnetic field region is deflected by the third effective magnetic field region and irradiates the isocenter at an irradiation angle θ relative to the X-axis, an arbitrary point P6 on a boundary defining the third effective magnetic field region and located on an exit side of a charged particle beam is positioned at the equal distance $r_1$ from the isocenter, the point P6 and a point P5 on a boundary defining the third effective magnetic field region and located on an incident side of a charged particle beam are on an arc of a circle of a radius $r_4$ and a central angle (θ+φ), and a distance R between the deflection point Q and the point P5 satisfies relational Equation (4b):

$$R = \sqrt{L^2 + r_1^2 - 2L(r_1\cos\theta + r_4\sin\theta)}, \quad (4b)$$

and wherein the second effective magnetic field region partially overlaps the first effective magnetic field region and the third effective magnetic field region.

7. The superconducting electromagnet apparatus according to claim 1 further comprising:

two or more power supply configured to supply current to and excite the first and second superconducting electromagnets; and a switching device that switches current supply from the power supply between the first and second superconducting electromagnets in accordance with the irradiation angle θ.

8. A charged particle irradiation apparatus comprising the superconducting electromagnet apparatus according to claim 1.

9. The charged particle irradiation apparatus according to claim 8 further comprising a bending magnet that deflects a charged particle beam from an accelerator at a deflection angle φ that is larger than or equal to 10 degrees at the deflection point Q.

* * * * *